（12）United States Patent
Wang et al.

(10) Patent No.: US 8,428,692 B2
(45) Date of Patent: Apr. 23, 2013

(54) SYSTEMS AND METHODS FOR BIOLUMINESCENT COMPUTED TOMOGRAPHIC RECONSTRUCTION

(75) Inventors: Ge Wang, Iowa City, IA (US); Eric Hoffman, Iowa City, IA (US); Geoffrey McLennan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 13/304,063

(22) Filed: Nov. 23, 2011

(65) Prior Publication Data

US 2012/0069958 A1     Mar. 22, 2012

Related U.S. Application Data

(63) Continuation of application No. 10/791,140, filed on Mar. 2, 2004, now Pat. No. 8,090, 431.

(60) Provisional application No. 60/453,177, filed on Mar. 10, 2003.

(51) Int. Cl.
*A61B 5/05* (2006.01)

(52) U.S. Cl.
USPC ............................ 600/425; 600/473; 600/476

(58) Field of Classification Search .................. 600/425, 600/473, 476
See application file for complete search history.

(56) References Cited

PUBLICATIONS

Warren et al. "Combined Ultrasound and Fluoresence Spectroscopy for Physico-Chemical Imaging of Atherosclerosis". IEEE Transactions on Biomedical Engineering 42(2) (1995): 121-132.*
Peter et al. "Design Study of a Novel Dual-Modality Emission Micro-Imaging Tomograph for Radiopharmaceutical and Bioluminescent/Fluorescent Molecular Approaches". IEEE Int'l Symp. on Biomedical imaging Proceedings (2002): 797-800.*

\* cited by examiner

*Primary Examiner* — Peter Luong
(74) *Attorney, Agent, or Firm* — Smith, Gambrell & Russell

(57) ABSTRACT

An image of an object is synergistically reconstructed using two or multiple imaging modalities. A first reconstructed image, showing structural information of the object is produced using a first imaging modality. The first reconstructed image is segmented, and known optical properties of the object are then mapped to the first reconstructed image. Optical signal emissions from the object are detected and registered with the first reconstructed image. A second reconstructed image volume is then produced using a second imaging modality, based on the mapped optical properties after registration between the first image and the data from the second modality. The second reconstructed image depicts some optical property, such as a bioluminescent source distribution, or optical properties, such as, attenuation and scattering properties, of the object.

20 Claims, 4 Drawing Sheets

Pulmonary Bioluminescence:
Visible from Multiple Angles of View

SYSTEMS AND METHODS FOR BIOLUMINESCENT COMPUTED TOMOGRAPHIC RECONSTRUCTION

CROSS-REFERENCE TO RELATED APPLICATION

This application is a continuation of U.S. patent application Ser. No. 10/791,140 filed Mar. 2, 2004, now U.S. Pat. No. 8,090,431 which claims priority from U.S. Provisional Application No. 60/453,177 filed Mar. 10, 2003, each of which are hereby incorporated by reference in their entirety.

BACKGROUND

This invention relates to multi-modality-based systems and methods for detecting an optical property distribution, such as a light-emitting source distribution, in multiple dimensions as well as systems and methods for reconstructing such an image from the detected signals from the distribution based on data from a tomographic imaging modality, including but not limited to computed tomography (CT) or micro-CT.

There are many "emission-detection" imaging techniques known in the art, such as bioluminescent imaging. However, such current imaging techniques are limited to the projective imaging mode or external excitation of the internal light source through external energy sources along selected paths. Therefore, three-dimensional structures and localization of an internally derived light source, such as one not reliant on external energy excitation, cannot be resolved with high quantitative accuracy both in terms of spatial location and localized activity.

Diffuse computed tomography (CT), another known imaging technique, computes distributions of absorption and scattering coefficients from scattered light through an object. Typically, intensity-modulated light sources are used. It is well known that diffuse CT will generally produce low image resolution, particularly as background heterogeneity increases.

It would therefore be desirable to combine an optical imaging technique, such as a light emission technique, specifically bioluminescent imaging, with a scanning technique that allows the evaluation of two and three dimensional structural information, such as computed tomography scanning or magnetic resonance imaging, to produce a reconstructed image having better image resolution.

SUMMARY

The present invention is directed to multi-modal imaging systems and methods that reconstruct images via fundamental and synergistic utilization of multi-model data. According to an exemplary embodiment, an image volume may be reconstructed in a first tomographic modality, optical properties from a database may be mapped to the image volume, and the image may then be reconstructed tomographically in another modality, based on the optical properties.

According to one embodiment, bioluminescent CT and CT/micro-CT combinations may be used, but other system configurations are possible. Some embodiments may include a magnetic resonance imaging (MRI) scanner or micro-MRI scanner in conjunction with a fluorescent tomographic scanner. The imaging techniques and algorithms described herein are exemplary only, and other methods of combining data from two or more tomographic scanners may be used.

Some embodiments may be capable of various resolutions depending on scanning times, possess extremely high photon detection sensitivity for mapping gene expression, and/or embody hardware and/or software technology for image reconstruction, registration, and analysis. Some embodiments may have the advantage of being configured to rapidly collect data with a higher signal-to-noise ratio.

According to one embodiment, bioluminescent imaging may be rendered in a two- or three-dimensional tomographic modality. In embodiments directed to bioluminescence, emitted photons can be collected from multiple three-dimensional directions with respect to an animal marked by bioluminescent compounds including reporter luciferases.

According to some embodiments, a CT or micro-CT scanner may be integrated with a bioluminescent imaging system. The bioluminescent imaging system may also be combined with other imaging systems which provide information regarding the distribution of tissue structures in vivo, in situ, or ex vivo.

In alternative embodiments, an object may be serially scanned using each modality in turn. In still further embodiments, the object may be transported between scanning modalities. Optionally, one or more registration marks may be placed on the object to coordinate positions between scanning modalities. The surface of the object may also be optically reconstructed for the registration purpose.

In some embodiments, information associated with x-ray CT imaging and bioluminescent imaging may be used together to estimate light scatter and/or other optical properties of tissue and thereby reconstruct a three-dimensional emission image volume registered to corresponding CT or micro-CT imaging of anatomical and pathological structures. As non-limiting examples, the system may be used to generate images of structures, such as bioluminescent sources, lungs and various tumors.

According to some embodiments, intra-organ localization of gene transcription activity may be performed with resolution capable of differentiating, for instance, gene expression in the central pulmonary airways (out to approximately the 5th-7th generation) versus parenchymal activity. Also, localization of parenchymal activity in terms of sub-lobar regions may be performed. As a non-limiting example, small animal imaging, in particular mouse imaging, may be performed. In other examples, the systems and methods may be used for other biomedical applications where bioluminescent signals are detectable. Some embodiments are especially suited for small animal imaging at molecular levels. For example, genetic activity in a particular organ system may be imaged.

By integrating x-ray and optical imaging, better optical tomography image quality can be achieved that would not be possible with a stand-alone optical system. From a corresponding x-ray CT image volume or image volume generated by other imaging energy sources, knowledge of the underlying distribution of optical scatters can be derived. This information is useful in reconstruction of images from optical data. Specifically, emitting source distributions may be directly solved for, obviating the need for reconstruction of optical properties in three dimensions.

According to exemplary embodiments, the combined use of x-ray CT and BLCT transforms the nonlinear optical CT problem into an easier linear problem. Therefore, the reconstruction of image data from a bioluminescent CT scanner may be significantly improved.

One embodiment includes a system processor that supports the desired functionality as described in detail below and a system data store (SDS) that stores data associated with the needed functionalities, such as image data and reconstruction. The system processor may be in communication with the SDS via any suitable communication channel(s).

The SDS may include multiple physical and/or logical data stores for storing the various types of information used. Data storage and retrieval functionality can be provided by either the system processor or one or more data storage processors associated with the SDS. The system processor may include one or more processing elements that are adapted or programmed to support the desired image storage, reconstruction and/or other functionality.

Accordingly, one method of image reconstruction includes a variety of steps that may, in certain embodiments, be executed by the environment summarized above and more fully described below or be stored as computer executable instructions in and/or on any suitable combination of computer-readable media. The steps can include but are not limited to performing tomographic reconstruction of an image volume in one modality, mapping optical properties to that volume from a database, and performing tomographic reconstruction in another modality based on the mapped optical properties.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DETAILED DESCRIPTION

Figure 1:
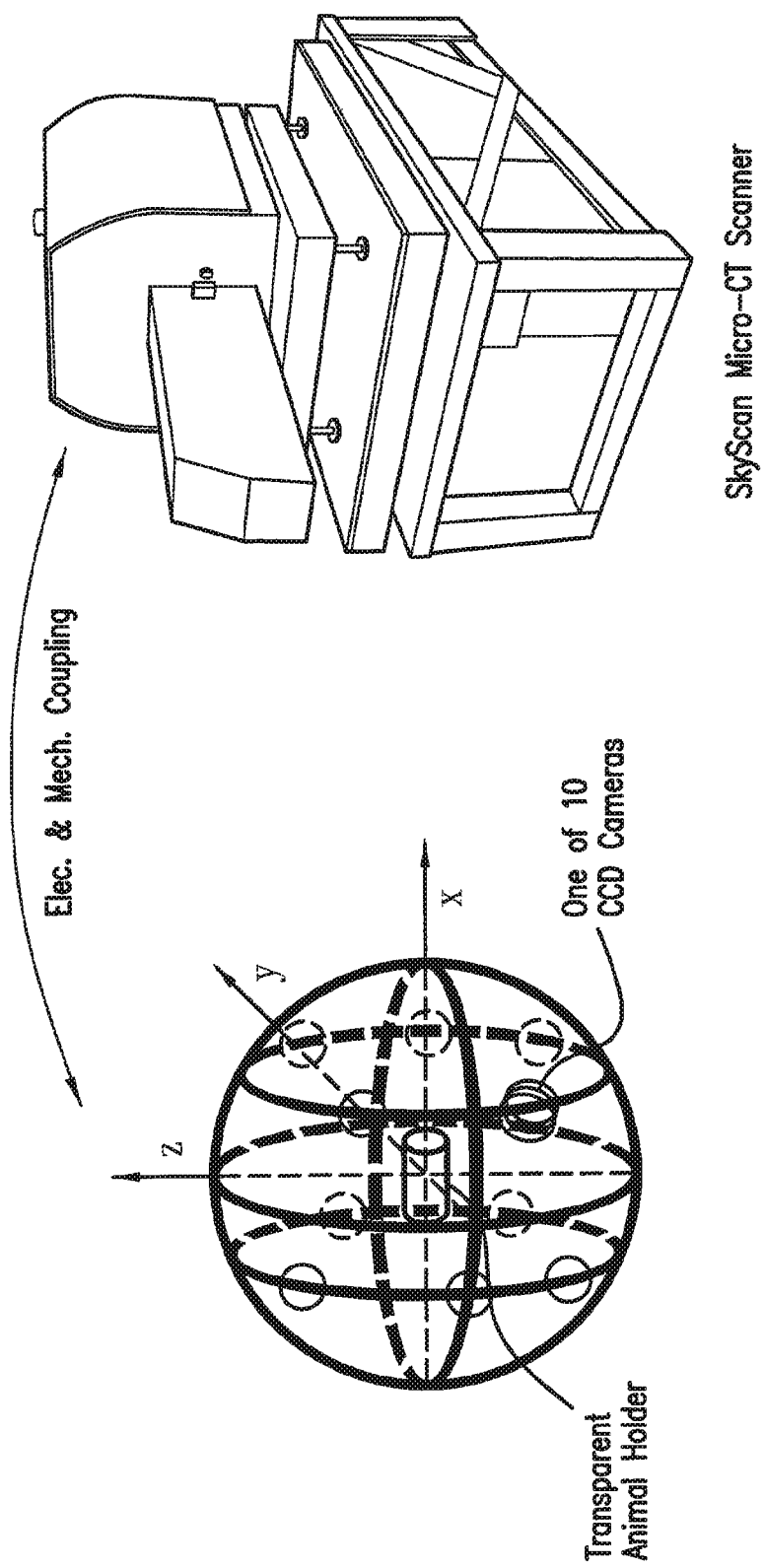
FIG. 1 depicts an exemplary bioluminescent imaging device (left panel) with an anatomic imaging device (micro CT scanner shown in the right panel).
Figure 2:
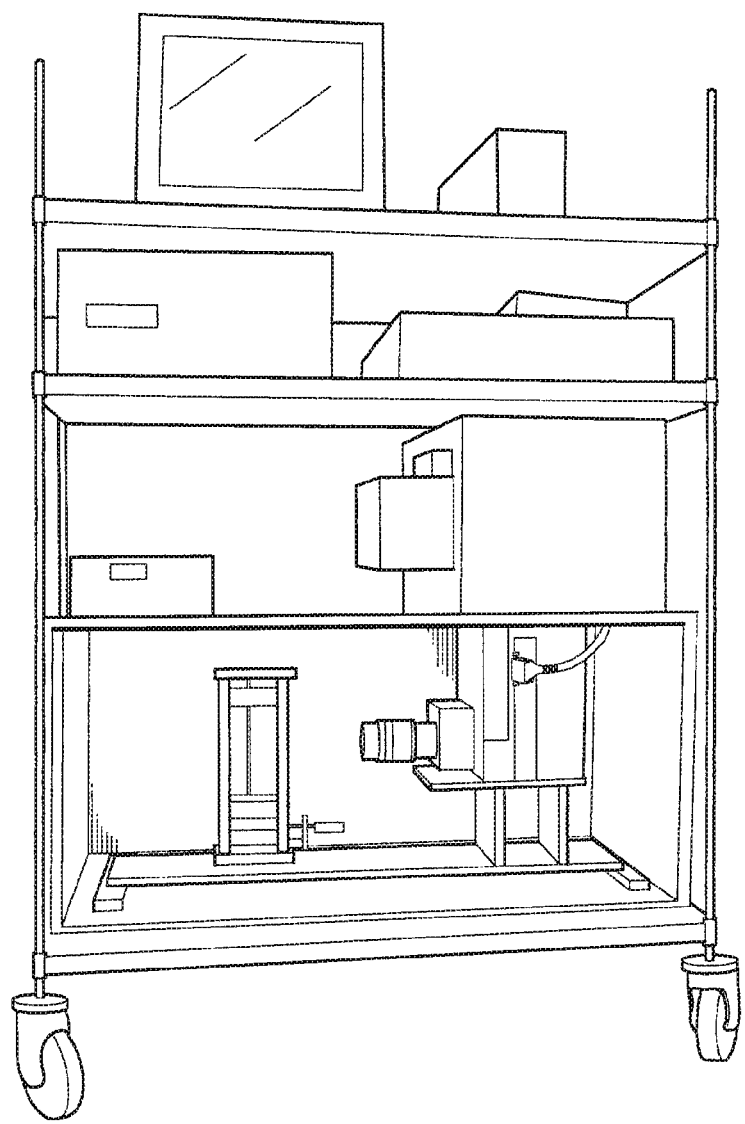
FIG. 2 depicts an exemplary single source bioluminescent CT scanner. The rotating stage and light sensitive camera is shown on the bottom shelf of the cart. The side of the light tight enclosure has been removed for system visualization.
Figure 3:
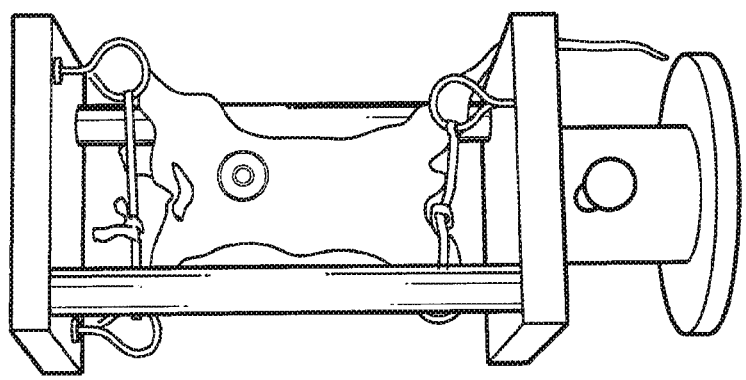
FIG. 3 depicts bioluminescence emitted from the lungs of a mouse following exposure to an adenovirus which has delivered the primary gene and reporter gene (producing luciferase) to the lungs. The emitted light can be seen from multiple angles according to exemplary embodiments. This is a precursor to being able to reconstruct the 3D distribution of the light source (s).
Figure 3:
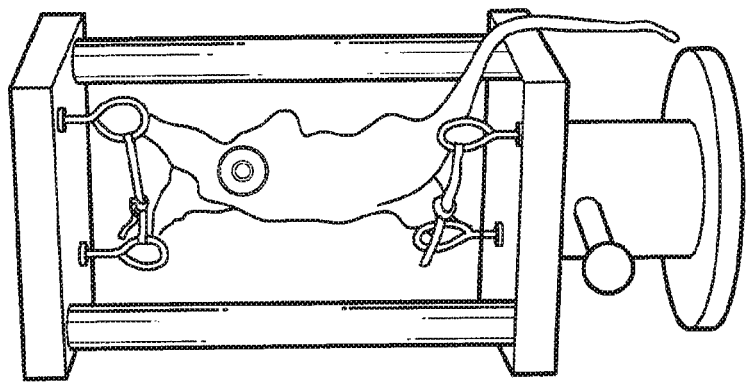
Figure 3:
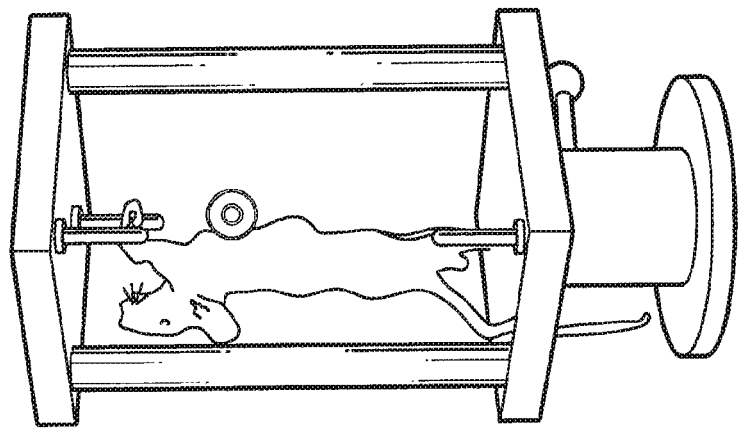
Figure 4:
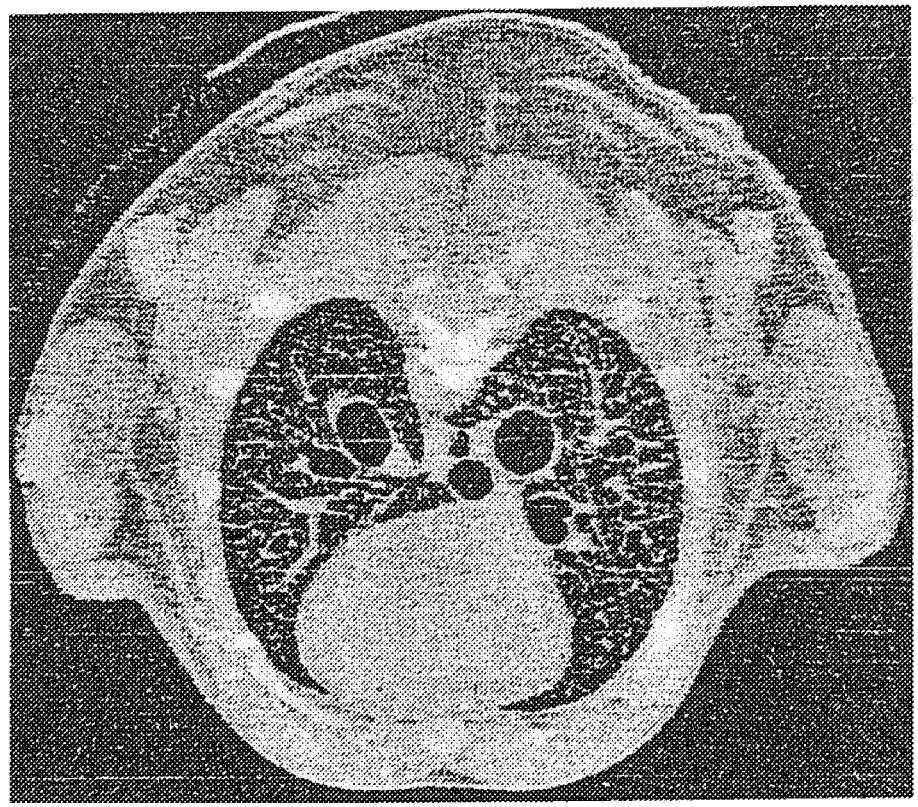
FIG. 4 depicts an exemplary micro-CT image of a lung showing structural components of the mouse thorax with resolution down to the alveolar level. This sort of anatomic image serves to provide the knowledge of the distribution of light scatterers.

One or more exemplary embodiments are now described in detail hereinbelow and in the attachments hereto. Referring to the drawings, like numbers indicate like parts throughout the views. As used in the description herein and attachments hereto, the meaning of "a," "an," and "the" includes plural reference unless the context clearly dictates otherwise. Also, as used in the description herein and attachments hereto, the meaning of "in" includes "in" and "on" unless the context clearly dictates otherwise. Finally, as used in the description herein and attachments hereto, the meanings of "and" and "or" include both the conjunctive and disjunctive and may be used interchangeably unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The present invention relates to systems and methods for detecting a light-emitting source distribution as well as systems and methods for reconstructing an image from the detected light signals and tomographic images obtained from one or more other modalities, such as an image volume from CT or micro-CT. Some embodiments may include one or more cameras arranged, e.g., symmetrically, on a spherical surface to detect a light emitting source distribution in three dimensions. Alternative embodiments may include asymmetrical camera arrangements and/or other three-dimensional surface arrangements. In some embodiments, other optical mechanisms can be used to intercept and direct signals to the cameras including, but not limited to, mirror and/or fiber systems.

Some further embodiments may detect and record bioluminescent emissions and/or fluorescent emissions. This image data, along with associated x-ray CT images of the same object, can be used to reconstruct a three-dimensional emission image volume and register the bioluminescent CT image to a corresponding x-ray CT or micro-CT image volume of anatomical and pathological structures. In some such embodiments, the bioluminescent (or fluorescent) reconstruction process can be enhanced through the use of knowledge gained from x-ray CT or other anatomic information gathered by use of other imaging devices including, but not limited to, MRI or ultrasound. As a non-limiting example, emitted photons can be collected from multiple directions in three dimensions with respect to a living animal or any other light emitting structure of interest marked by bioluminescent reporter luciferases or fluorescent sources. In some embodiments, a lung and/or various tumors may be imaged.

According to exemplary embodiments, optical properties of an object are presumed to be already known, and the photon-emitting source distribution may be computed based on these known optical properties. Therefore, the imaging models for the systems and methods according to exemplary embodiments are approximately linear, while that for the conventional techniques, such as diffuse CT, are nonlinear and correspondingly more difficult to solve.

By combining a system for detecting light emission from multiple angles of view simultaneously or sequentially with an imaging modality which allows the evaluation of two and three dimensional structural information, such as micro x-ray CT, the anatomic and/or structural details gained from the micro x-ray CT can be used to estimate the distribution of light scattering structures for purposes of directing the computed tomographic calculations required to create BLCT cross-sectional or volumetric images. Such a system may enable, as non-limiting examples, both the calculation of the computed tomograms of chemo-luminescence and the linking of the computed tomograms of chemo-luminescence to the highly detailed anatomic image sets derived from the x-ray CT imaging. In some embodiments, the tomographic reconstruction of bioluminescence can provide important added detail regarding regional location of reporter gene activity. By knowing the location of reporter gene activity and having micro-resolution images of anatomy, a user can follow the link between gene activation and pathologic processes.

Typical Storage and Processing Architecture

In one exemplary embodiment, the imaging and reconstruction system includes a system processor potentially including multiple processing elements. The term processing element may refer to (1) a process running on a particular piece, or across particular pieces, of processing hardware, (2) a particular piece of processing hardware, or either (1) or (2) as the context allows. Each processing element can be supported via a standard general purpose processor such as an Intel-compatible processor platforms preferably using at least one CELERON, PENTIUM, XEON, ITANIUM (Intel Corp., Santa Clara, Calif.) class processor; alternative processors such as MIPS (MIPS Technologies, Mountain View, Calif.) or UltraSPARC (Sun Microsystems, Palo Alto, Calif.) could be used in other embodiments. The system processor, or the one or more processing elements thereof, can include one or more field programmable gate arrays (FPGAs), programmable digital signal processors (DSPs) and/or application specific integrated circuits (ASICs) configured to perform at least a portion of the functionality according to the present invention. In other embodiments, an embedded microprocessor can be used such as, but not limited to, an ARM (ARM, Carlsbad, Calif.) processor core.

In some embodiments, the system processor can include a combination of general purpose processors, ASICs, DSPs and/or FPGAs. In some embodiments, the systems and methods of the present invention, as described above, can be distributed across multiple processing elements. In some such embodiments, aspects of the functionality or portions thereof may be executed in series or in parallel; particular functionality or portions thereof executed a multiplicity of times may also occur in series or parallel.

In a system processor including at least one general purpose processor, the general purpose processor typically runs an appropriate operating system such as WINDOWS/NT, WINDOWS 2000 or WINDOWS/XP (Microsoft, Redmond, Wash.), IRIX (Silicon Graphics, Mountain View, Calif.), SOLARIS (Sun Microsystems, Palo Alto, Calif.), or LINUX (or other UNIX variant). In one embodiment, the Windows 2000 operating system is used.

The SDS may include a variety of primary and secondary storage elements. In one embodiment, the SDS can include random access memory (RAM) as part of the primary storage; the amount of RAM might range from 512 MB to 4 GB in some embodiments. The primary storage can, in some embodiments, include other forms of memory such as cache memory, registers, non-volatile memory (e.g., FLASH, ROM, EPROM, etc.), etc.

The SDS can also include secondary storage including single, multiple and/or varied servers and storage elements. For example, the SDS can use internal storage devices connected to the system processor. In embodiments where a single processing element supports all of the system functionality, a local hard disk drive can serve as the secondary storage of the SDS, and a disk operating system executing on such a single processing element can act as a data server receiving and servicing data requests. A system bus can serve as the communication channel between the system processor and the SDS (typically, at least RAM and the hard disk drive).

It will be understood by those skilled in the art that the different information used in the imaging and image reconstruction processes and systems according to the present invention can be logically or physically segregated within a single device serving as secondary storage for the SDS; multiple related data stores accessible through a unified management system, which together serve as the SDS; or multiple independent data stores individually accessible through disparate management systems, which may in some embodiments be collectively viewed as the SDS. The various storage elements that comprise the physical architecture of the SDS may be centrally located or distributed across a variety of diverse locations.

The architecture of the secondary storage of the system data store may vary significantly in different embodiments. In several embodiments, database(s) are used to store and manipulate the data; in some such embodiments, one or more relational database management systems, such as DB2 (IBM, White Plains, N.Y.), SQL Server (Microsoft, Redmond, Wash.), ACCESS (Microsoft, Redmond, Wash.), ORACLE (Oracle Corp., Redwood Shores, Calif.), Ingres (Computer Associates, Islandia, N.Y.), MySQL (MySQL AB, Sweden) or Adaptive Server Enterprise (Sybase Inc., Emeryville, CA), may be used in connection with a variety of storage devices/file servers that may include one or more standard magnetic and/or optical disk drives using any appropriate interface including, without limitation, ATA, IDE and SCSI. In some embodiments, a tape library such as available from Exabyte Corporation (Boulder, Colo.), a storage attached network (SAN) solution such as available from EMC, Inc. (Hopkinton, Mass.), a network attached storage (NAS) solution such as available from Network Appliances (Sunnyvale, Calif.), or combinations thereof may be used. In other embodiments, the data store may use database systems with other architectures such as object-oriented, spatial, object-relational or hierarchical.

Instead of, or in addition to, those organization approaches discussed above, certain embodiments may use other storage implementations such as hash tables or flat files or combinations of such architectures. Such alternative approaches may use data servers other than database management systems such as a hash table look-up server, procedure and/or process and/or a flat file retrieval server, procedure and/or process. Further, the SDS may use a combination of any of such approaches in organizing its secondary storage architecture.

The SDS communicates with the system processor by one or more communication channels. Multiple channels can be involved in some embodiments for supporting communication between processing elements of the system processor and portions of the SDS. Such channels can include without limitation computer network, direct dial-up connection, dedicated connection, direct or indirect connection such as via a bus connection, parallel or serial connection, USB connection, null modem connection or wireless connection utilizing an appropriate communication protocol such as BLUETOOTH, IRDA, 802.11b or other suitable channel as would be known to those skilled in the art.

All forms of data, including raw, intermediate, and computed can be stored on one or more SDS either temporarily or permanently. In particular, the SDS can store, without limitation, image data, including volumetric image data, reconstruction intermediate data, final reconstructed imaging data, imaging parameters, and reconstruction parameters. Further, the SDS may, in some embodiments, store instructions for performing the various imaging and reconstruction tasks, or portions of such tasks.

Light Sensitive Cameras

In one embodiment, ten CCD cameras can be arranged at the center of each identical face of a dodecahedron, except for the two facing the front and back ends of an object to be imaged. Each of the 10 cameras can point to the iso-center where the object can be fixed on a holder. The imaging geometry can be implemented by a structure holding each camera in its fixed position. Data from the cameras can be transmitted to one or more processing elements for further processing and image reconstruction. A light-free housing can be used to house the imaging cameras. Once the frame of the imaging device is arranged, a camera can be mounted at any spot of the 12 nominal positions on the dodecahedron. One or more cameras can be geometrically and photographically calibrated with reference phantoms. An optical surface scanner can be combined with the imaging frame for the registration purpose.

One skilled in the art will recognize that other arrangements of cameras are possible, including geometrically symmetrical and asymmetrical configurations, with or without appropriate optical paths such as obtained through use of minors or fiberoptic relay paths. In some embodiments, one or more cameras can be rotated around an object of interest. Alternatively, or in combination, the subject of the imaging can be rotated on one or more axis. As a non-limiting example, such embodiments can be used in cases where light emission is unstable. In this case, dynamic bioluminescent and/or fluorescent tomographic imaging would be feasible.

In one embodiment, one or more cooled back-thinned integrating CCD cameras can be used for imaging. The camera package can include a 2.2 L or other appropriately sized end-on liquid nitrogen dewar for cooling. Alternatively, an omni-directional dewar can be used to allow cameras to be mounted in any orientation while keeping the dewar right-side up. In some embodiments, the imagers can be sensitive to one or more bioluminescent sources of different spectral characteristics. Other types of light sensitive cameras can also be used. Analog films can be used with appropriate manipulations.

A living organism, or other structure of interest, can be scanned using a multi-detector spiral CT, another appropriate method of imaging known to one skilled in the art, or a micro x-ray CT scanner. From this imaging, a distribution of optical properties of the object can be derived to guide associated bioluminescent and/or fluorescent tomographic imaging.

Camera Control

According to exemplary embodiments, one or more camera control elements may be used. A camera control element can include one or more processing elements and can be in communication with the SDS. The imaging cameras of the present invention can be in communication with the one or more camera control elements. Camera control elements can perform digitization of output from cameras and other processing as appropriate. Relevant imaging parameters can be controlled by the camera control elements. As non-limiting examples, imaging parameters such as focus, exposure time, aperture, can be configured. Additional parameters known to one skilled in the art can also be configured as appropriate.

In some embodiments, all cameras can be controlled by a single controller element. In other embodiments, a single controller element may be used to control multiple cameras. In such an embodiment, cameras may be arbitrarily grouped into arrays and each array can be controlled by a single controller element. Each camera acquisition chain can then operate independently. Still further embodiments can include a master controller element to provide control and synchronization for an entire camera array. In one embodiment, one camera is controlled by a single controller element. One skilled in the art will recognize that other configurations of cameras and controller elements are possible.

Some embodiments can include one or more hierarchies of control elements and/or processing elements. Different levels of hierarchy can perform the same or different functions. In one embodiment, images from low-level camera control elements are passed to higher level processing elements and/or control elements for additional processing and/or image reconstruction, as further described below. Control elements and processing elements can be communicatively coupled via any suitable communication means including computer network, wired or wireless direct link, bus connection and as further described below.

In one embodiment, individual cameras can be controlled with an external camera control element in communication with a PCI controller card in communication with one or more processing elements. The PCI controller card and the camera control element can be communicatively coupled via an RS-422 link or other suitable serial or parallel connection. The external camera control element and the camera can be communicatively coupled via a parallel interface. In one such embodiment, cameras output analog signals which are digitized by one or more external camera control elements. To minimize noise, the length of the link between the camera and the controller box can be minimized.

In one embodiment, the light-emitting source data acquisition process can include one or more of the following steps: (1) reset and/or initialize cameras; (2) execute a programmable, configurable, or manual shutter open on one or more cameras; (3) execute a programmable, configurable, or manual shutter close on one or more cameras; (4) transfer image data to one or more camera control elements, processing element, or SDS; and (5) store the images in the SDS. Additional embodiments can have shutter times configured to occur simultaneously across multiple cameras and/or automatically after a predetermined time delay.

Image Reconstruction Using an Iterative Method or Other Methods

Given the ill-posed nature of the imaging and sampling geometry, an iterative image reconstruction approach may be used utilizing prior knowledge on the distribution to be reconstructed. The iterative approach can be used in the case of incomplete and/or noisy data. Also, the iterative approach easily accommodates prior knowledge and imaging physics.

An interface from one or more camera control elements and/or processing elements to one or more reconstruction engines can be provided. The systems of the present invention can acquire optical properties of the object being imaged and then compute the light-emitting source distribution based on the optical properties. Therefore, the imaging model is approximately linear. In one embodiment, x-ray CT data is used to regularize the BLCT reconstruction problem and transform it from a nonlinear one to linear one and thereby greatly simplify it.

Even with attenuation and scattering taken into account based on a CT or micro-CT image volume, a discrete BLCT imaging model can still be linearly expressed as $Ax=b$, where the observed data $b=(b^1, \ldots, b^M) \in R^M$, original emitting source distribution $x=(x_1, \ldots, x_M) \in R^N$, and a known non-zero M×N matrix $A=(A_{ij})$. The coefficients of the matrix A depend on the anatomical structures and their optical properties according to the classic Radiative Transfer Equation (using the Monte Carlo method) or the well-known diffusion approximation or another appropriate method. The systems and methods according to exemplary embodiments can reconstruct the image x from the data b.

A generalized BLCT algorithm according to one embodiment can include one or more of the following steps: (1) reconstruction and segmentation of an x-ray CT image volume, (2) association of optical properties to each segmented region in the x-ray CT volume based on a library of optical properties, (3) determination of coefficients of the forward imaging matrix $A=(A_{ij})$ based, e.g., on Monte Carlo simulations, (4) reconstruction of the emitting source distribution x by inverting the matrix A, subject to the constraints imposed by the segmented anatomical structures, their properties, and known features of the underlying source distribution (such as the homogeneity or parametric form of the source distribution, the shape or intensity of the source). According to exemplary embodiments, bioluminescent emissions, and well as other light-emitting source distributions, such as fluorescent source distributions, may be detected and reconstructed in this way or another alternative way.

As non-limiting examples, the optical properties of step two can include absorption coefficients, scattering coefficients, scattering anisotropy, indices of refraction, and other appropriate parameters known to one skilled in the art. Monte Carlo simulations can be used to predict bioluminescent signals and construct the matrix A based on the CT/micro-CT image volume of the object. Other methods, such as finite element methods and meshfree methods, may be also used for this purpose. After image segmentation, optical properties can be assigned to each segment based on a library of optical properties.

In one embodiment, both the ordered-subset expectation maximization (OS-EM) and the ordered-subset version of the simultaneous algebraic reconstruction technique (OS-SART) schemes for BLCT can be implemented. A roughness penalty method for BLCT or other method known to one skilled in the art can also be used.

Although an iterative method may be most suitable to the image reconstruction task in one embodiment, other image reconstruction methods can be used. Even further, the iterative procedure described above is only an example, and should not be interpreted as a limiting description.

As far as image reconstruction methods are concerned, it is emphasized that there are multiple options or possibilities. In addition to an iterative reconstruction strategy as described above, numerical solutions to the Radiative Transfer Equation or its approximation, such as the diffusion equation, can be useful as well. A fast analytic method would be very useful in practice. In one embodiment, an analytic approach known as the Kirchhoff approximation may be adapted for bioluminescent tomography of diffuse media with an embedded source distribution. Other numerical methods, such as finite element methods and/or meshfree methods, are also feasible for the same purpose.

CT/Micro-CT Scanner

Any state-of-the-art micro-CT scanner can be used according to exemplary embodiments. In some embodiments, the ImTek MicroCAT II described, e.g., at http://www.imtekinc.com/html/microcat_ii_specifications.html, or the SkyScan-1076 in-vivo micro-CT system described, e.g., at http://www.skyscan.be/next/spec_1076.htm, can be used.

In other embodiments, the data acquisition system can include one or more of the following items: a dedicated embedded data acquisition and control computer, two 130 kVp ultra-high resolution µfocus X-ray systems, two 100/50 mm dual-field image intensifiers, and two 2048×2048 CCD cameras. The scanner can include one or more processing elements in communication with the SDS, a multi-axis precision scanner and specimen manipulator with linear servo drives, remotely configurable motorized source-detector geometries, a signal and power slip ring for continuous rotation, and a means to move data between acquisition and processing. The slip ring can have two independent capacitively coupled data transmission channels with full-duplex fibre channel interfaces. The one or more processing elements, the slip ring data channels and the SDS can be communicatively coupled. In one embodiment, they can be connected via one or more fiber optic cables.

One embodiment may be built on an optical grade table for vibration isolation and precision alignment. An imaging chain of source arrays, detector arrays, and accessories, alone or in combination, can be mounted on a rotating plate which is in turn supported by an open bearing and rigid stand. The axis of rotation can set to any appropriate angle including vertical and horizontal. The geometry of each imaging chain can be individually configured to suit a wide variety of operating modes. Each x-ray tube and image intensifier can be moved radially, while each image intensifier can also be moved laterally. The object can rest horizontally in a holder mounted to a linear axis with a certain amount of axial travel room for slice positioning. One exemplary embodiment is capable of achieving spatial resolution of 100 lp/mm for excised samples, and temporal resolution of 1.8 seconds for objects up to 120 mm in diameter. The system can be configured to allow a wide range of intermediate combinations of scan time and spatial resolution.

System Integration

The light-emitting source distribution CT device and the anatomic imaging scanner, such as a micro x-ray CT scanner, can be electronically and mechanically integrated but need not be in all embodiments. In one embodiment, the hardware structures of the two imaging units can share a table and/or a holder attached to a table. This embodiment can allow the translation of an object for x-ray CT scanning to be extended into the light-emitting CT device in a precise and/or repeatable fashion. Some embodiments may be configured to optimize and integrate software packages for Monte Carlo simulation (another kind of simulation, such as that based on finite element computation), CT and/or micro-CT data preprocessing and reconstruction, BLCT reconstruction, image visualization and analysis. A user interface to perform and/or to configure such functions can also be provided in some embodiments; in some such embodiments, the user interface can further allow viewing of results and may allow control of parameters with respect to such viewing. Any software capable of performing such functions can be implemented on one or more processing elements.

Exemplary Applications

The following applications are intended as illustrative examples only and are not limiting of the invention. According to exemplary embodiments, advanced imaging, such as lung imaging, is enabled in that the structural and function information can be obtained concurrently at the molecular level, and can be evaluated on a regional, sub-lobar basis. This combination allows simultaneous examination of gene expression and anatomic structures and improves understanding of the human lungs.

Exemplary embodiments may be used in gene therapy imaging, to probe the distribution of the administered gene, reporter genes, such as those producing luciferase, can be included in the transfecting virus. These genes cause the emission of light, enabling the functional gene to be identified within the target tissue.

Exemplary embodiments may also be useful in evaluating transgene expression in the lung; gene transfer vectors; gene transfer to the respiratory epithelium of mice; in vivo bioluminescence imaging; understanding the site of transgene expression in the lung; human lung lobe imaging and sheep-based emphysema model evaluation; understanding the site of gene therapy, and its consequences; and understanding the pathophysiology of airway vs. alveolar infection.

The embodiments described above are given as illustrative examples only. It will be readily appreciated by those skilled in the art that many deviations and other applications may be made from the specific embodiments disclosed in this specification without departing from the scope of the invention.

What is claimed is:

1. A system, comprising:
    X-ray imaging equipment for imaging an object to produce a reconstructed image;
    bioluminescence imaging equipment comprising a camera housed in a light-free housing and configured to detect bioluminescent signals emitted from the object, the bioluminescence imaging equipment being further configured to:
        map optical properties of the object to the reconstructed image, the map step yielding mapped optical properties of the object and
        reconstruct a bioluminescent source distribution of the object based at least on the mapped optical properties.

2. The system of claim 1, wherein the camera is a cooled back-thinned charge-coupled device (CCD) camera.

3. The system of claim 1, wherein the X-ray imaging equipment is tomographic X-ray imaging equipment.

4. The system of claim 1, wherein the bioluminescence imaging equipment is further configured to detect the bioluminescent signals emitted from the object in three dimensions.

5. The system of claim 3, wherein the bioluminescence imaging equipment is further configured to detect substantially sequentially the bioluminescent signals emitted from the object at multiple angles.

6. The system of claim 3, wherein the bioluminescence imaging equipment is further configured to detect sequentially the bioluminescent signals emitted from the object at multiple angles of view.

7. The system of claim 1, wherein the cooled back-thinned CCD camera is in communication with a control element configured to control said camera.

8. The system of claim 7, wherein the control element is further configured to control at least one imaging parameter of the cooled back-thinned CCD camera, the at least one imaging parameter comprising one or more of a focus, an exposure time, or an aperture.

9. The system of claim 1, wherein the optical properties comprise at least one of absorption coefficients, indices of refraction, scattering coefficients, or scattering anisotropy.

10. The system of claim 1, wherein the bioluminescent source distribution is produced using a radiative transfer equation or an approximation to the radiative transfer equation.

11. A method, comprising:
    acquiring X-ray imaging data from an object to produce a reconstructed image of the object;
    detecting bioluminescence emitted from the object;
    mapping optical properties of the object to the reconstructed image of the object; and
    reconstructing a bioluminescent source distribution of the object based at least on mapped optical properties, wherein the bioluminescent source distribution is produced using a radiative transfer equation or an approximation to the radiative transfer equation.

12. The method of claim 11, wherein the detecting step comprises collecting said bioluminescence at a plurality of locations arranged on a surface surrounding the object.

13. The method of claim 11, wherein the detecting step comprises detecting substantially simultaneously bioluminescence emitted from multiple angles of view.

14. The method of claim 11, wherein the detecting step comprises detecting sequentially bioluminescence emitted from multiple angles of view.

15. The method of claim 11, wherein supplying data for mapping the optical properties of the object to the reconstructed image of the object comprises supplying data for estimating the scattering properties and the optical absorption properties of the object.

16. An apparatus, comprising:
    means for acquiring X-ray imaging data from an object to produce a reconstructed image;
    means for detecting bioluminescence emitted from the object;
    means for mapping optical properties of the object to the reconstructed image of the object; and
    means for reconstructing a bioluminescent source distribution of the object based at least on mapped optical properties.

17. The apparatus of claim 16, wherein the bioluminescent source distribution is produced using a radiative transfer equation or an approximation to the radiative transfer equation.

18. The apparatus of claim 16, wherein the means for detecting the bioluminescence emitted from the object comprises means for collecting said bioluminescence at a plurality of locations arranged on a surface surrounding the object.

19. The apparatus of claim 16, further comprising means for rotating the object about at least one axis.

20. The apparatus of claim 16, further comprising means for moving the object among a location associated with the means for acquiring X-ray imaging data and a location associated with the means for detecting bioluminescence emitted from the object.

* * * * *